Figure 1:
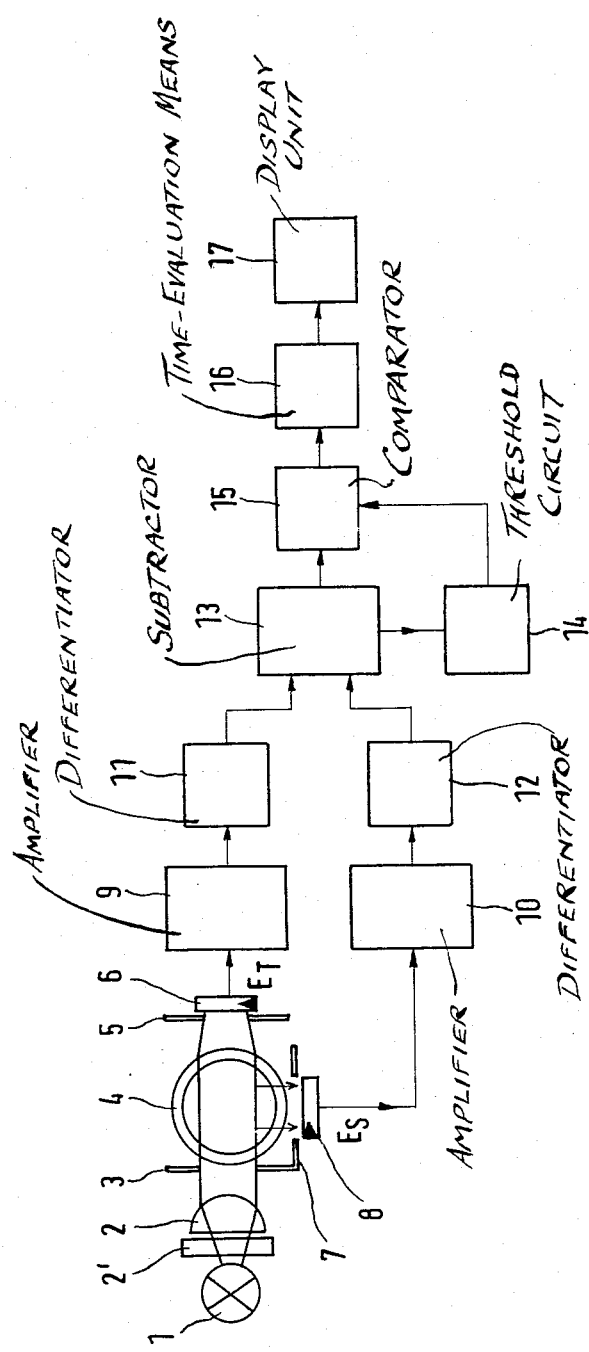

United States Patent [19]

Pross et al.

[11] Patent Number: 4,492,462
[45] Date of Patent: Jan. 8, 1985

[54] PHOTOMETRIC METHOD FOR DETERMINING COURSES OF REACTIONS

[76] Inventors: Wilhelm Pross, Oberstdorfer Str. 8, 8000 München 71; Jürgen Barry, Ludmillastr. 13, 8000 München 90; Franz Mühlböck, Gabriele-Münter Str. 9, 8000 München 71; Klaus Hartmann, Südliche Auffahrtsallee 68, 8000 München 19, all of Fed. Rep. of Germany

[21] Appl. No.: 234,573

[22] Filed: Feb. 13, 1981

[30] Foreign Application Priority Data

Feb. 16, 1980 [DE] Fed. Rep. of Germany ....... 3005923

[51] Int. Cl.³ ............................................. G01N 33/48
[52] U.S. Cl. ..................... 356/39; 73/64.1; 356/339; 356/342; 356/436
[58] Field of Search .................. 356/338–343, 356/434–435, 442, 436, 39, 72, 73; 350/73, 39; 73/64.1

[56] References Cited

U.S. PATENT DOCUMENTS

| | | | |
|---|---|---|---|
| 3,027,461 | 3/1962 | Kavanagh | 356/341 |
| 3,518,437 | 6/1970 | Riggs | 356/343 |
| 3,658,480 | 4/1972 | Kane et al. | 356/39 |
| 3,680,962 | 8/1972 | Hayakawa | 356/343 |
| 3,746,869 | 7/1973 | Lindstedt et al. | 356/73 |
| 3,785,735 | 1/1974 | Friedman et al. | 356/432 |
| 4,193,692 | 3/1980 | Wynn | 356/343 |
| 4,252,536 | 2/1981 | Kishimoto et al. | 73/64.1 |

Primary Examiner—Bruce Y. Arnold
Attorney, Agent, or Firm—Townsend and Townsend

[57] ABSTRACT

The invention provides a photometric method of determining courses of reaction in a specimen, in which method the intensities of the transmitted light and of the stray light are measured, wherein the two intensities are measured simultaneously and the electrical signals corresponding to the transmitted light and to the stray light are combined to form one signal. The invention makes it possible to perform reliable measurement even with low levels of transmitted and stray light.

The method is preferably used in determining the coagulation times of blood. Apparatus for carrying out the method is also disclosed.

8 Claims, 9 Drawing Figures

PHOTOMETRIC METHOD FOR DETERMINING COURSES OF REACTIONS

The invention relates to a photometric method of determining courses of reaction in a specimen, in which method the intensities of the transmitted light and of the stray light are measured.

Furthermore, the present invention relates to a photometric apparatus for determining courses of reaction in a specimen, which apparatus comprises a light source, a specimen container, a first photoelectric transducer on which the transmitted light impinges and which is disposed at that side of the specimen container which is remote from the light source, and a second photoelectric transducer on which the light scattered in the specimen impinges.

Photometric methods and photometric apparata of the kind described initially for, for example, determining and investigating the coagulation time and the coagulation process of the blood are known from, for example, U.S. Pat. Nos. 4,116,564 and 3,593,568 and British Patent Specification No. 908,050. In these known specifications, the transmitted light passing through the specimen is measured and is evaluated for the purpose of ascertaining the coagulation. The level of light measured is relatively low, particularly in the case of low values of the transmitted light, so that the measured values lie in the noise level of the apparatus or in the vicinity thereof, and thus contain only a low level of information. Furthermore, interference effects, such as fluctuations in the intensity of the light source, radiation of ambient light or mixture streaks in the specimen can affect the order of magnitude of the measuring effects and thus falsify the measured values. Moreover, the changes in the translucence are frequently only slightly pronounced in pathological plasmas as a result of the formation of fibrin, so that difficulties arise when determining the occurrence of coagulation optically.

A method and an apparatus in connection with the determination of the coagulation time of blood are also known from German Offenlegungsschrift No. 28 48 552, in which the stray light is measured. In contrast to the method in which transmitted light is used, the level of stray light is greater in the case of high opacity and thus the measurement of the opacity or the particle concentration, in this case with stray light, is more reliable. Conversely, when the particle concentration and thus the scatter in the specimen are low, the level of stray light does not lie above the noise level, or only slightly above the noise level; in this case, reliable measurement cannot be performed. Furthermore, the interference effects already mentioned for the transmission signal again take effect when only the stray light is measured.

German Offenlegungsschrift No. 28 36 607 describes a measuring system for determining oil pollution in water, in which system a stray light measurement is performed with a relatively low concentration of oil, since, in the case of a low concentration of oil, the stray light signal is affected to a substantially lesser extent than the transmitted light by other impurities such as sand and rust. On the other hand, if the concentration of the oil globules in the water is greater, the damping of the light becomes greater than the stray effect, and measurement with stray light is rendered inaccurate in this system. For this reason, in the known measuring system, automatic change-over from stray light measurement to transmission light measurement is effected when the oil concentration reaches a predetermined value. However, the known measuring system again involves mutually independent measurements with stray light and with transmitted light, so that these measurements exhibit the disadvantages already mentioned.

A photometric method and photometric apparatus for absorption measurement are known from German Offenlegungsschrift No. 27 57 197 in which the absorption measurement is performed with transmitted light. In order to prevent the absorption measurement with transmitted light from being affected by any opacities present, the light scattered by any unwanted opacity is intercepted at a predetermined angle simultaneously with the actual absorption measurement and, in dependence upon this, a warning signal is given or the absorption measurement is interrupted. However, the stray light is not measured, and only the occurrence of stray light is ascertained. The stray light is thereby not used to improve the measurement method itself.

The object of the present invention is to provide a photometric method and a photometric apparatus which render it possible to perform reliable measurement even with low levels of transmitted light or stray light and to prevent or compensate for interference effects occurring during the measurement.

Proceeding from the known methods and apparatus mentioned initially, and in accordance with the invention, this object is achieved in that the two intensities are measured simultaneously and the electrical signals corresponding to the transmitted light and to the stray light are combined to form one signal.

In photometric measurement, either the level of transmitted light or the level of stray light usually predominates according to the opacity or the concentration, size and/or shape of the particles in the specimen. Therefore, without knowledge of the behaviour of the specimen, reliable results can only be obtained in some cases (the most favourable cases) by the known method. By virtue of the method in accordance with the invention, that is to say, measuring the level of the transmitted light and measuring the level of the stray light and then combining the corresponding electrical signals to form one signal, it is possible to perform a reliable measurement in both cases. Exhaustive tests in connection with the present invention showed that it is thereby possible to at least double the signal-to-noise ratio.

Numerous photometric measurements have shown that, according to requirements, the noise level, interference level or peaks are intensified on one of the two signals during measurement, and the other signal is substantially free from interference. This applies particularly to the transmitted light in the case of mixture streaks in the specimen and to the stray light in the case of effects of the ambient light. A useful signal of relatively high amplitude is produced by inverting one of the signals and then adding it to the other signal to form one signal, the interference level or noise peaks then being relatively low. Thus, the reliability of measurement is thereby increased. In the event of interference effects which affect the level of the transmitted light and the level of the stray light, such as in the case of varying or fluctuating intensity of the light source, such interference can be compensated-for by combining the mutually opposing output signals of the photoelectric transducers.

In accordance with a preferred embodiment, the electrical signals corresponding to the transmitted light and to the stray light are subtracted.

The signals corresponding to the transmitted light and to the stray light are preferably differentiated before the subtraction operation, particularly when changes in the opacity or in the particle concentration or in the shape of the particles in a specimen are to be determined. This is advisable particularly when specific points are to be ascertained in the opacity curve, such as the so-called pipetting drop or the coagulation point, when determining the coagulation time of blood.

In accordance with an advantageous development of the invention, the output signals of the two photometric transducers are amplified before the differentiating operation or before the subtraction operation. In this connection, it is particularly advantageous to perform standard amplification by which the signal-to-noise ratio of the combined signal can be further increased, even to the extent that it can be at least doubled again.

In accordance with an important alternative development of the method in accordance with the invention, the two electric values corresponding to the transmitted light and the stray light are multiplied. Thus, the expenditure on circuitry for processing the two output signals of the first and second photoelectric transducers can be further reduced, and advantages accrue with respect to the optimum shape of the combined signal for the evaluation.

Advantageously, there is provided in the last-mentioned embodiment in accordance with the invention a current-voltage transducer (C/V transducer) to one input of which is applied the output signal of one of the two photoelectric transducers which is constituted by a photoelement, the other photoelectric transducer, such as a photoresistor, being located in the feedback circuit of the C/V transducer. This renders it possible to simplify the circuitry with the result that instantaneous single-channel further processing of the signal is achieved. The C/V transducer then makes a signal available which is formed by multiplying the output signal of one of the photoelectric transducers by the inverted value of the other photoelectric transducer, that is to say, by multiplying the transmitted light signal by the inverted stray-light signal.

In a further advantageous embodiment of the invention, the stray light is measured at an angle of from 90° to 180° (backscatter) relative to the transmitted light, preferably at an angle of 100° relative to the transmitted light.

Furthermore, it is advantageous to mask the stray light in the forward direction in the vicinity of the transmission beam by a diaphragm, to prevent the stray light from being superimposed on the transmission beam and thus to prevent the signal in the transmission channel from being impaired by the stray light.

Moreover, it is advantageous to pick up the scattered light for the stray-light channel preferably in the vicinity of the light entry to the specimen container at the start of the absorption path, in order to minimize the overlapping effect reducing the change of level of the stray light, of the light absorption in the specimen and thus to intensify the measuring effect in the stray light channel.

The method in accordance with the invention, the apparatus in accordance with the invention, and the above-mentioned advantageous developments of the same, are particularly suitable for determining the coagulation times of blood.

The invention will be described hereinafter with reference to the drawings and in connection with the determination of blood coagulation time, although the method in accordance with the invention and the apparatus in accordance with the invention can also be used to advantage in the case of other photometric measurements such as determining oil pollution in water, detecting faults in absorption photometry or in the monitoring of gelatinization processes.

Figure 2A:
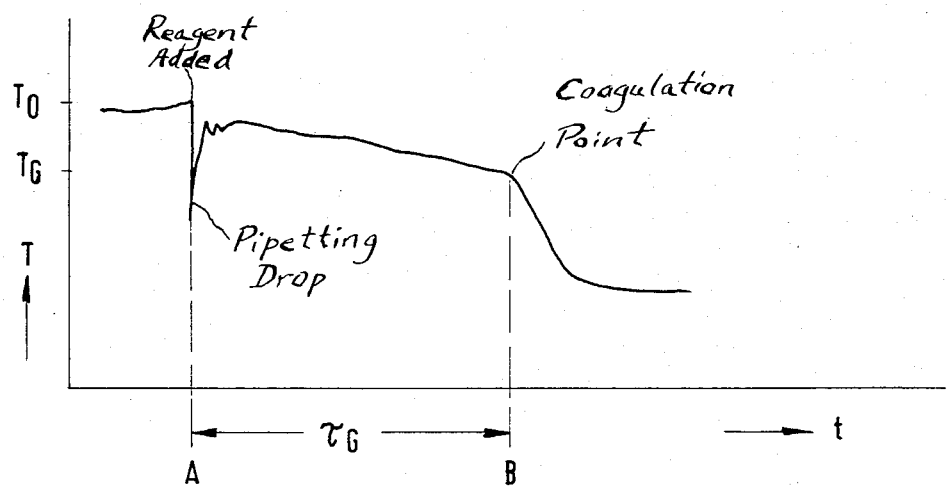
Figure 2B:
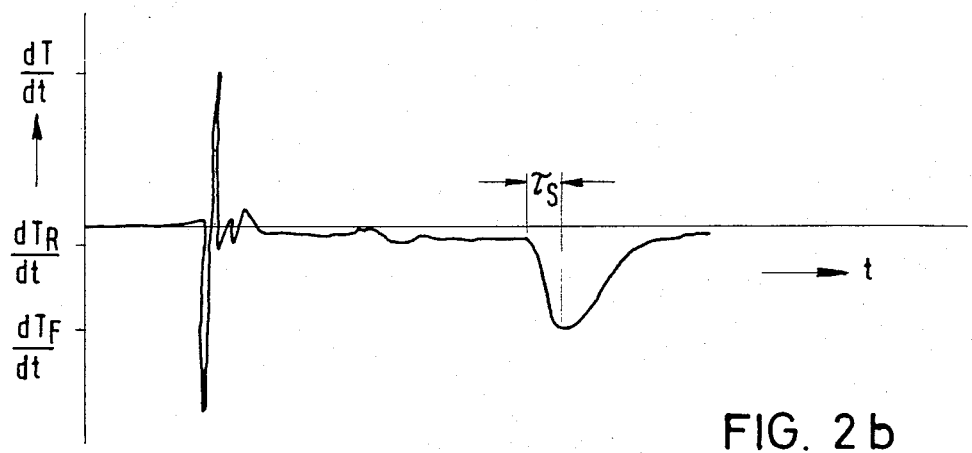
Figure 3A:
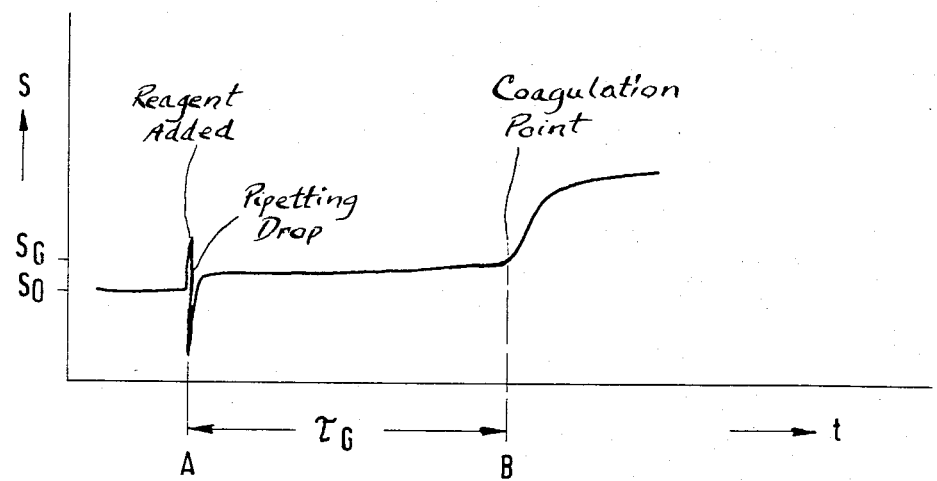
Figure 3B:
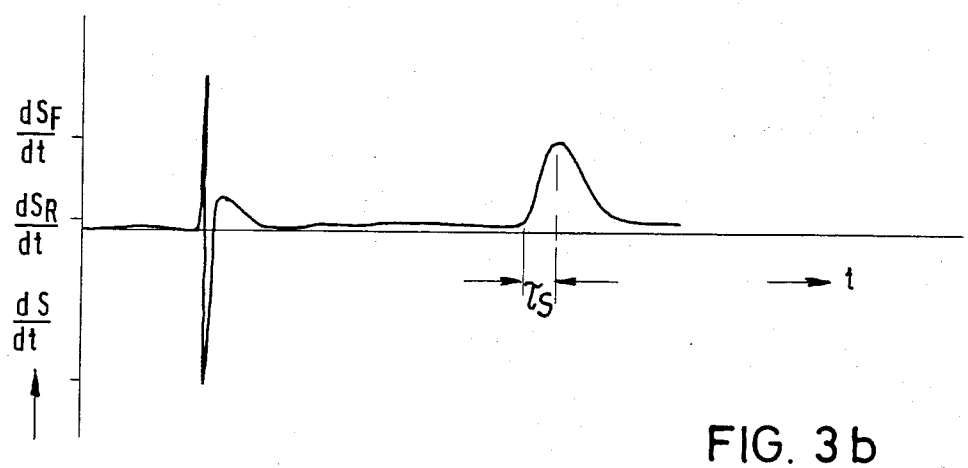
Figure 4:
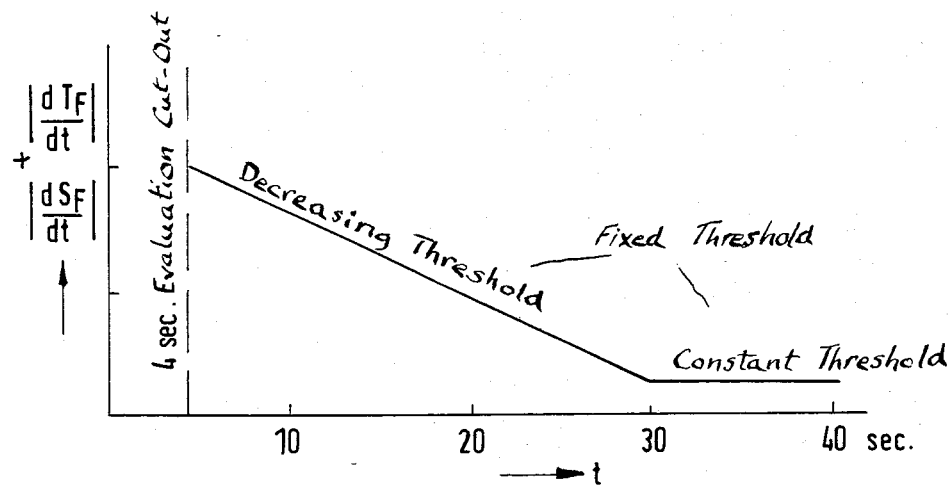
Figure 5:
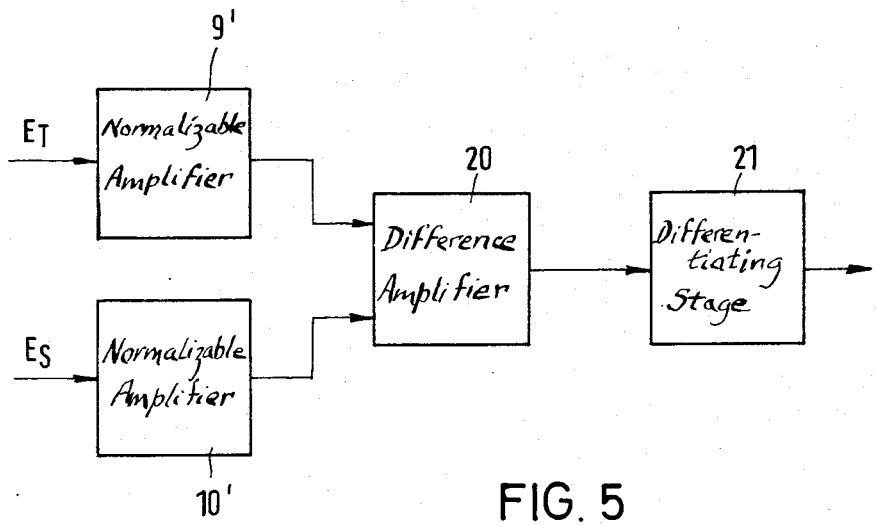
Figure 6:
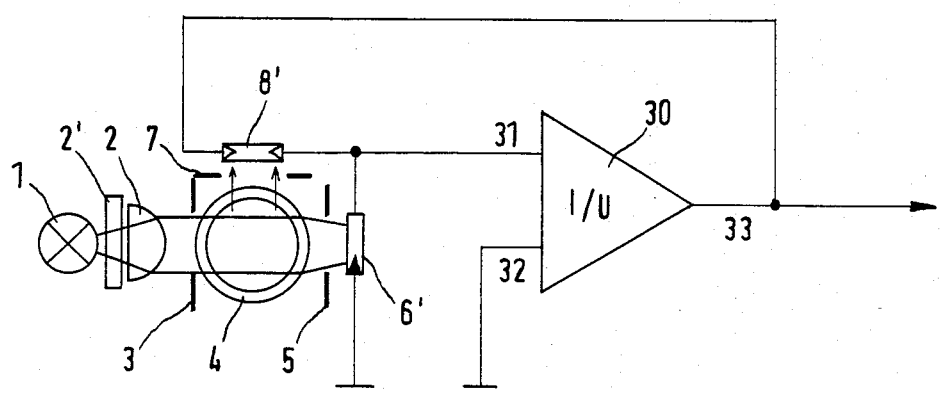
Figure 7:
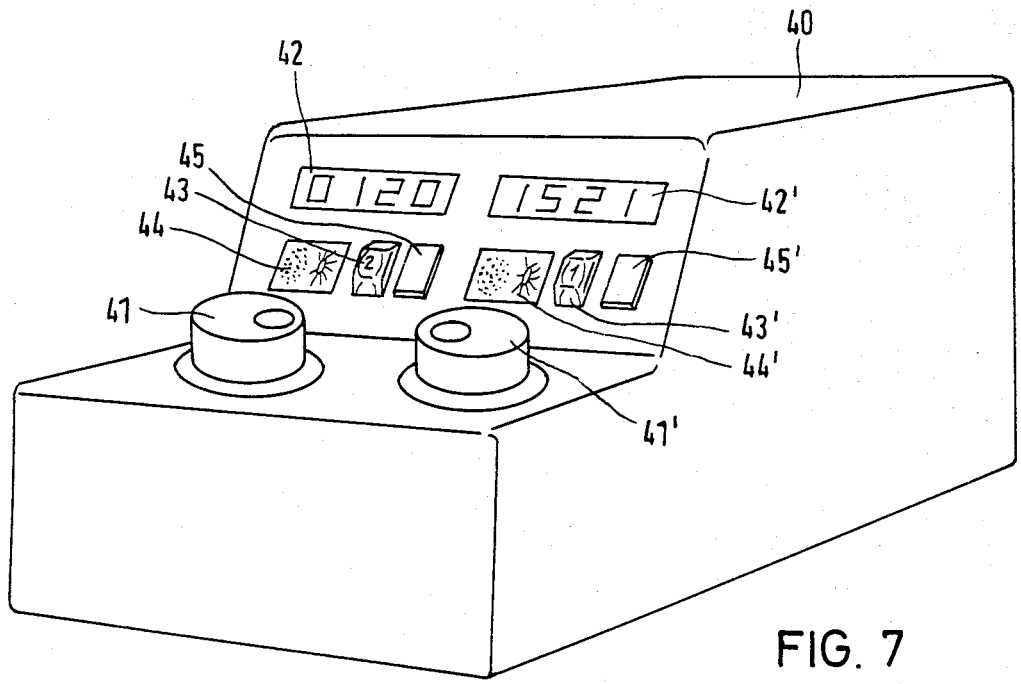

In the drawings:

FIG. 1 is a diagrammatic illustration of a preferred embodiment of a photometric apparatus in accordance with the invention, FIGS. 2a and 2b show the characteristic of the transmission signal and the characteristic of the differentiated transmission signal respectively, when determining the coagulation time, FIGS. 3a and 3b shows the characteristic of the stray light signal and the characteristic of the differentiated stray light signal, when determining the coagulation time, FIG. 4 is a threshold value curve for preventing transient phenomena from interfering with the course of the measurement, FIG. 5 shows a further advantageous embodiment of a portion of the signal-processing circuit, FIG. 6 is a diagrammatic illustration of the photometric apparatus in accordance with a further preferred development of the invention, and FIG. 7 is a diagrammatic illustration of an apparatus for optical coagulation analyses, in accordance with one embodiment of the invention.

FIG. 1 is a diagrammatic illustration of a photometric arrangement comprising a light source, 1, a condenser 2 which effects parallel alignment of the light coming from the light source, an entry diaphragm 3, a specimen container 4, a first photoelectric transducer 6, a transmission exit diaphragm 5 disposed between the specimen container 4 and the first photoelectric transducer 6, a second photoelectric transducer 8, and a stray light exit diaphragm 7 disposed between the specimen container 4 and the second photoelectric transducer 8. The first photoelectric transducer 6 supplies an output signal constituted by an electrical signal $E_T$ corresponding to the level of the transmitted light, and the second photoelectric transducer supplies an output signal constituted by a stray light signal $E_S$ corresponding to the level of the stray light.

The determination of the coagulation time of blood is used as an example for the purpose of explaining the present invention with reference to a practical operation. Determination of the coagulation time of blood is a particularly important photometric measurement in which special procedures have to be observed and for which the photometric method in accordance with the invention and the photometric apparatus in accordance with the invention are particularly suitable.

The amplitude of the transmission signal is plotted against time t in FIG. 2a.

By way of example, citrate plasma, which has been obtained from whole blood by centrifuging, is used as the starting specimen. The plasma specimen is incubated at 37° C. A specific reagent is added at the instant A (see FIGS. 2a, 2b, 3a, 3b) to initiate coagulation. A so-called pipetting drop thereby occurs in the characteristic of the transmission signal and in the characteristic of the stray light signal (see FIGS. 2a and 3a) and decays and merges into a continuous signal characteristic. A bend, the so-called coagulation point, appears in the signal characteristic at the instant B and is caused by the first appearance of fibrin clots.

When determining the coagulation time, the instant A at which the reagent initiating coagulation is added is ascertained as the starting point, and the instant B at which coagulation commences, that is to say, the instant at which the coagulation point occurs, is ascertained as the end point. These instants A and B can be ascertained from the change in the transmission signal or from the change in the stray light signal. The period of time between the instant A and the instant B, that is to say, between the instant at which the reagent is added and the instant at which the coagulation point occurs, is the coagulation time $\tau_G$. Referring to FIG. 2a, $T_O$ represents the level of transmission at the termination of incubation before the reagent is added, and $T_G$ represents the level of transmission at the coagulation point, $T=100\%$ being defined as the level of transmission in the case of a specimen container filled with water.

Referring to FIG. 3a, $S_O$ represents the level of stray light at the termination of incubation, $S_G$ represents the level of stray light at the coagulation point, and $\tau_G$ represents the coagulation time. Darkness, that is to say, the stray light level O, is defined by $S=0\%$, the level of stray light in the case of a specimen container filled with water is defined by $S: 5\%$, and the stray light level of a specific reagent is defined by $S: 70\%$.

The transmission light level alone, or the stray light level alone would not lead to evaluable signals in many cases, particularly when the plasma or blood to be tested photometrically differs substantially from healthy plasma or blood (such as lipaemic or haemophilic plasma), so that the conventional photometric method cannot be used for this purpose. Measurement of the coagulation time in critical cases, and in the case of specimens differing greatly from the norm, is possible only by combining the transmitted light and stray light signals. Changes in the transmitted light level or stray light level of the specimen also occur as a result of adding the reagent. These effects are compensated for in the present design of the apparatus, so that aspects of optical measurement technology do not have to be taken into account when choosing the reagent, and the reagent can be chosen entirely according to medical diagnostic requirements.

As will be seen from FIGS. 2a and 2b, a steady change in the level of transmitted light or the level of stray light can occur during the reaction time, that is to say, between adding the reagent and the occurrence of the coagulation point. Thus, changes in slope have to be used for ascertaining the instants A and B in order to be able to make a statement about the instant of coagulation.

The differentiated transmission signal characteristic dT/dt and the differentiated stray light signal characteristic dS/dt are shown in FIGS. 2b and 3b respectively. In FIG. 2b, $dT_R/dt$ represents the slope before the coagulation point, $dT_F/dt$ represents the maximum slope after the coagulation point, and $\tau_S$ represents the slope rise time. In FIG. 3b, $dS_R/dt$ represents the slope before the coagulation point, $dS_F/dt$ represents the maximum slope after the coagulation point, and $\tau_S$ represents the slope rise time. The slope exist in the differentiated signal as absolute values in %/sec.

The transmitted light signal and the stray light signal are differentiated in differentiators 11 and 12 respectively (see FIG. 1). The output signals of the photoelectric transducers 6 and 8 have previously been amplified in the amplifiers 9 and 10 respectively.

The plasma specimens and the various reagents initiating coagulation show very great differences in the range of the transmitted light level and in the range of the stray light level, and small slope values result for low levels in the case of the differentiated signal. Therefore, it is advantageous to use normalizable amplifiers instead of conventional amplifiers 9 and 10 in order to obtain normalization amplification of the output signals of the photoelectric transducers 6 and 8 and to obtain a uniform level shortly after the reagent has been added, that is to say, after approximately 3 seconds. Thus, reference levels independent of the choice of the reagent and independent of the properties of the specimen are obtained for further evaluation.

Tests in connection with the photometric measurement of the coagulation time of blood have shown that slight changes in slope, which have nothing to do with the commencement of coagulation, occur after the pipetting addition, particularly in the case of the transmitted light signal and in contrast to the stray light signal. These changes in slope independent of the commencement of coagulation are smaller in the stray light signal.

By means of the method in accordance with the invention, that is to say, combining the stray light signal and the transmitted light signal to form one signal, it is possible to eliminate or substantially reduce, in a convenient manner, the interference effects and factors to which the transmitted light level and the stray light level are subjected to different extents, which would not be possible if only the transmitted light level or only the stray light level were evaluated during photometric determination of the coagulation time.

The output signals of the differentiators 11 and 12 are fed to a subtractor 3 in which the differentiated transmitted light signals and stray light signals are subtracted. This results in the advantages, already described in detail, of the present invention, that is to say, in short, that evaluable signals can still be produced even in critical cases and the measured values can be determined with increased reliability, since, as already mentioned, interference effects are frequently present in only one of the two signals or occur to a greater extent in one of the two signals than in the other signal and, moreover, the measuring effects are greater in either the transmitted light signal or in the stray light signal according to the existing special case.

As already mentioned, and as will be seen in FIGS. 2a, 2b and 3a and 3b, considerable fluctuations, which decay with time, occur in the transmitted light signal and in the stray light signal after the reagent has been added. In a specific embodiment, to prevent the measured values and the measurement method from being impaired by these "transient oscillations", an evaluation cut-out, relative to a threshold value curve, is provided, such as is shown by way of example in FIG. 4. The formation of the threshold value, which will be further described hereinafter, is effected by the circuit portion 14 of FIG. 1. The large initial oscillations in the two signals are rendered ineffective by means of an evaluation cut-out of, for example, 4 seconds (see FIG. 4). A fixed threshold decreasing with respect to time is provided in order to prevent the measurement from being effected after the instant A by dying out of these oscillations and the changes of slope, already mentioned, in the transmitted light signal. A delayed signal threshold derived from the differentiated primary signal can also be provided in addition to this fixed threshold. Therefore, the circuit 14 illustrated diagrammatically in FIG. 1 is connected to the subtractor 13. In order to eliminate signal portions which interfere with the measurement and which do not relate to the actual measurement, the output signal of the subtractor 13 is compared in the threshold comparison stage 15 with the threshold value characteristic made available by the threshold value formation stage 14. The output signals are formed in a time evaluation stage 16 connected to the output of the threshold value comparison stage 15 and are fed to a display unit 17.

Preferably, the photoelectric transducer 8 for measuring the stray light and/or the stray light exit diaphragm 7 are disposed such that the light impinges on the second photoelectric transducer 8 for measuring the stray light at an angle of from 90° to 180° relative to the first photoelectric transducer 6. A particularly advantageous angle between the first and second photoelectric transducer 6 and 8 is an angle of 100°.

The forward scatter, that is to say, the stray light in the ambiency of the beam of transmitted light, is masked by the transmitted light exit diaphragm 5, and thus a less affected level of the transmission signal is obtained.

The effect of the absorption path opposing the level of the stray light is minimised by a stray light mask which, advantageously is disposed in the vicinity of the light entry to the vessel, so that the level of the stray light remains substantially unaffected thereby.

FIG. 5 shows a further advantageous development of an important part of the apparatus in accordance with the invention which replaces the amplifiers 9, 10, the differentiators 11, 12 and the subtractor 13 of FIG. 1. In the embodiment illustrated in FIG. 5, the transmission light signal $E_T$ coming from the first photoelectric transducer 6 is fed to a normalizable amplifier 9', and the stray light signal $E_S$ coming from the second photoelectric transducer 8 is fed to a normalizable amplifier 10'. The measure whereby the amplifiers 9 and 10 are replaced by normalizable amplifiers 9' and 10' has already been described and explained. Instead of the subtractor 13 of FIG. 1, the present embodiment of FIG. 5 incorporates a differential amplifier 20 which constitutes a subtractor for performing the subtraction operation. The output of the differential amplifier 20 is connected to a differentiating stage 21 which performs the differentiation analogously or digitally according to requirements. The other parts of the circuit and the other elements correspond to those of FIG. 1, and have therefore been omitted from FIG. 5. The arrangement illustrated in FIG. 5 is simpler and can be realised with fewer circuit elements. The output range of the differential amplifier can be matched to approximately 2×25% of the input range by raising the transmitted light signal and the stray light signal to the same level (for example, to 75%) by the normalizable amplifiers 9' and 10', which corresponds to quadrupling the resolution. High demands with respect to stability are placed on the circuit arrangement of FIG. 1, since the signals produced in these circuit elements must not be affected by, for example, the effects of ageing or temperature. When the circuit arrangement is of analog construction, high stability of this kind can only be realised at great expense. Alternatively, the signals after the differentiating stage 21 can be further processed digitally in order to avoid problems connected with possible drift, and to avoid complicated analog circuit portions for the delayed signal threshold and the fixed threshold. Basically, it is also possible to use a microprocessor for digital processing.

FIG. 6 shows a particularly advantageous embodiment of the photometric apparatus in accordance with the invention. The elements 1 to 5 and 7 in FIG. 6 correspond to those provided with the same reference symbols in FIG. 1. A photoelement 6' in FIG. 6 is provided as the first photoelectric transducer 6, and a photoresistor 8' in FIG. 6 is provided as the second photoelectric transducer. The transmission light impinges on the photoelement 6' and the stray light impinges on the photoresistor 8'. One terminal of the photoelement 6' is connected to one input 31 of an C/V transducer 30 whose other input 32, like the other terminal of the photoelement, is connected to earth.

One terminal of the photoresistor 8' is connected to the input 31 and the other terminal of the photoresistor 8' is connected to the output 33 of the C/V transducer. Thus, the photoresistor 8' constitutes a feedback resistor in the feedback circuit of the C/V transducer. The photoresistor 8' serves as stray light detector and its resistance value is dependent upon the level of the stray light. Thus, there appears at the output of the C/V transducer 30 a signal which corresponds to the transmitted light signal multiplied by the inverted stray light signal.

By virtue of the arrangement shown in FIG. 6 a substantially simpler circuit can be obtained for the combined detection of the measured values of the transmitted light signal and the stray light signal, with the advantage of single-channel further processing.

Preferably, the wavelength of the light used for photometric measurement should be chosen in dependence upon the scatter cross section of the particles. As is shown in FIG. 1 this can be effected by a filter 2' in the incident light. In another, preferred embodiment (not illustrated), filtering can be effected on the reception side in advance of the photoelectric transducers, and, in particular, opens up the possibility of separate filtering in the transmission light channel and in the stray light channel in the preferred wavelength range of from 350 to 550 nm. This results in amplification of the transmitted light signal and the stray light signal. A suitable wavelength is obtained by appropriate filtering.

FIG. 7 is a diagrammatic illustration of a layout of an embodiment of a coagulation time meter 40 in accordance with the present invention. This apparatus is designed for two measuring locations 41, 41' for receiving the specimen containers. Each measuring location 41, 41' has an associated display device 42, 42' respectively.

Before the actual measurement is undertaken, the incubation time is set by a preselector switch 43, 43'. Signal generators 44, 44' indicate the end of the incubation period. The measuring operation proceeds automatically after the reagent has been added, the optical signals being processed in the evaluation unit in the manner described. The results of the measuring operation or the blood coagulation time are displayed optically in the display units 42 and 42' respectively. Intervention during or after the measuring operation is rendered possible by way of a reset button 45, 45'.

The present invention has been described with reference to embodiments in connection with the measurement of the coagulation time of blood. However, without departing from the essentials of the invention, these embodiments can be developed and modified in a large number of ways by one skilled in the art. In particular, the method in accordance with the invention, and the apparatus in accordance with the invention can also be applied to photometric measurements for other purposes, such as for determining oil pollution in water, for detecting faults in absorption photometry and when monitoring gelatinisation processes.

We claim:

1. A photometric method for determining the coagulation time of a sample, said sample including blood mixed with a reagent, comprising:
    detecting the intensity of a light beam transmitted through said sample and forming an electrical signal proportional thereto;
    detecting, at an angle of from 90 to 180 degrees to the transmitted light beam, the intensity of light scattered by said sample and forming an electrical signal proportional thereto;
    combining said electrical signals to form a combined signal;
    from said combined signal, determining the coagulation time of said sample.

2. A method as claimed in claim 1, in which the electrical signals corresponding to the transmitted light beam and to the scattered light are subtracted.

3. A method as claimed in claim 1, in which the electrical signals corresponding to the transmitted light beam and to the scattered light are differentiated and then subtracted to obtain the combined signal.

4. A method as claimed in claim 1, in which the electrical signals corresponding to the transmitted light and to the scattered light are multiplied to obtain the combined signal.

5. A method as claimed in claim 1, in which the scattered light is measured at an angle of 100° to the transmitted light beam.

6. The method of claim 1, wherein there is included the step of masking the stray light in the vicinity of the region at which the transmitted light beam leaves the region in which scattering occurs.

7. A method as claimed in claim 1, in which the wavelength of the light is chosen in dependence upon the absorption- and/or the scatter behaviour of the particles causing the opacity.

8. A method as claimed in claim 1, in which the maximum of the wavelength of the detected light lies in a range of wavelength of from 350 nm to 550 nm.

* * * * *